United States Patent [19]

Huang et al.

[11] Patent Number: 5,070,213

[45] Date of Patent: Dec. 3, 1991

[54] PERFLUORO-4,4'-BIS(2,2-DIMETHYL-1,3-DIOXOLANE) AND ITS PREPARATION AND USE

[75] Inventors: Hsu-Nan Huang, Newark; Ming-Hong Hung; Carl G. Krespan, both of Wilmington, all of Del.

[73] Assignee: E. I. Du Pont de Nemours and Company, Wilmington, Del.

[21] Appl. No.: 568,810

[22] Filed: Aug. 17, 1990

[51] Int. Cl.$^5$ .......................................... C07D 317/32
[52] U.S. Cl. .................................... 549/448
[58] Field of Search .......................... 549/448

[56] References Cited

U.S. PATENT DOCUMENTS 4,496,749 1/1985 Squire ................................ 549/448

Primary Examiner—Nicky Chan

[57] ABSTRACT

The novel compound perfluoro-4,4'-bis(2,2-dimethyl-1,3-dioxolane) is disclosed. Its preparation by fluorination of 4,4'-bis[2,2-bis(trifluoromethyl)-1,3-dioxolane using UV radiation or by reaction of 2,2-bis(trifluoromethyl)-4-iodo-4,5,5-trifluoromethyl-1,3-dioxolane with zinc in acetic anhydride and methylene chloride is also disclosed. The infusion of perfluoro-4,4'-bis(2,2-dimethyl-1,3-dioxolane) into mammalian tissue to facilitate inspection thereof by nuclear magnetic resonance imaging is also disclosed.

1 Claim, No Drawings

PERFLUORO-4,4'-BIS(2,2-DIMETHYL-1,3-DIOXOLANE) AND ITS PREPARATION AND USE

FIELD OF THE INVENTION

The present invention relates to perfluoro-4,4'-bis(2,2-dimethyl-1,3-dioxolane), its preparation from 4,4'-bis[2,2-bis(trifluoromethyl)-1,3-dioxolane] by reaction with fluorine using ultraviolet light as catalyst or by reaction of 2,2-bis(trifluoromethyl)-4-iodo-4,5,5-trifluoro-1,3-dioxolane with zinc in acetic anhydride and methylene chloride.

The use of the compound perfluoro-4,4'-bis-(2,2-dimethyl-1,3-dioxolane) in magnetic resonance imaging is also a part of the present invention.

PRIOR ART

Nuclear magnetic resonance (NMR) has been used for many years to ascertain the structure of chemical compounds containing atoms, mainly hydrogen, having the proper spin when placed in an applied magnetic field. Magnetic resonance imaging (MRI) or NMR imaging has only recently been used to map the internal structure of tissues and organs of mammals. It does this by providing a cross-sectional display of a body organ with excellent resolution of soft tissue detail. The images produced constitute a map of the distribution density of protons and/or their relaxation times in organs and tissues.

The use of perfluorocarbon compounds in various diagnostic imaging technologies such as ultrasound, magnetic resonance, radiology and CT has been described in an article by Robert F. Mattrey in SPIE, Vol. 626, Medicine, XIV/PACS, IV (1986), pgs. 12-23.

The use of MRI on liver tumors in rats using perfluorochemical emulsions is disclosed in "In Vivo $^{19}$F NMR Imaging of Liver, Tumor and Abscess in Rats", H. E. Langmaid, III, et al., Investigative Radiology, March-April, 1985, Vol. 26, pgs. 141-144.

European published patent application 0 118 281 discloses a technique for detection of gas in an animal using NMR and various fluorochemical agents.

Multiresonance perfluorocarbon emulsions (Oxyphenol and Fluorosol-DA) are disclosed for imaging tumors in mice using $^{19}$F spin-echo MRI in vivo by R. P. Mason et al.; Magnetic Resonance Imaging, 1989, Vol. 7, pgs. 175-485.

U.S. Pat. No. 4,838,274 discloses a method for $^{19}$F MRI wherein the improvement is the use of perfluorinated 15-crown-5-ether,

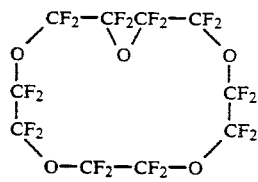

This compound has 20 magnetically similar fluorine atoms providing a superior signal to noise ratio when used in MRI.

U.S. Pat. No. 3,324,144 discloses the reaction of fluorinated ketones with epoxides in the presence of catalytic amounts of alkali metal or quanternary ammonium halides.

U.S. Pat. No. 4,725,342 discloses vapor phase dimerization of alkanes, saturated ethers, saturated primary alcohols and silanes induced by photoactivated mercury.

Brown and Crabtree, J. Chem., Educ., 1988, 65, pgs. 290-294, discloses the above dimerizations plus those of saturated amines and $CF_3CH_2OH$.

U.S. Pat. No. 4,496,749 discloses oligomers of perfluoro(2,2-dimethyl-1,3-dioxole) having the formula

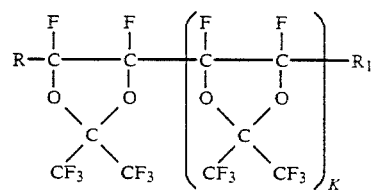

where K is 1-4, R and $R_1$ are fragments of the radical causing chain initiation and termination such as hydrogen or an ether residue.

SUMMARY OF THE INVENTION

One aspect of the present invention is a method for obtaining fluorine magnetic resonance images of body organs or tissues by administering to a mammal an aqueous emulsion of the novel fluorine 25 containing agent perfluoro-4,4'-bis(2,2-dimethyl-1,3-dioxolane) in sufficient amounts to provide fluorine magnetic resonance images of such organs or tissues and imaging said organs or tissues. Preferably, the perfluoro-4,4'-bis(2,2-dimethyl-1,3-dioxolane) is administered as an aqueous isotonic emulsion having a fluorochemical concentration of 5 to 40 v/u. The fluorochemical emulsion generally is administered to the mammal by direct injection into a body part, a body compartment, the bloodstream.

DETAILED DESCRIPTION OF THE INVENTION

The present invention relates to the compound perfluoro-4,4'-bis(2,2 -dimethyl-1,3-dioxolane) i.e., PBDD which has the formula:

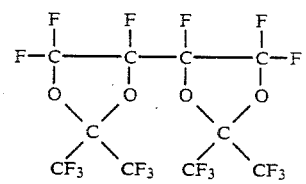

Two methods have been discovered for the preparation of the subject compound. The first of these methods involves the fluorination of 4,4'-bis [2,2-bis(trifluoromethyl)-1,3-dioxolane] using ultraviolet light as catalyst. The reaction proceeds as follows:

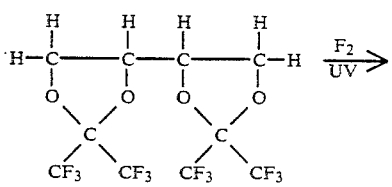

-continued

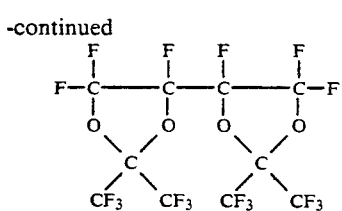

The 4,4'-bis[2,2-bis(trifluromethyl)-1,3-dioxolane] has previously been made from butediene dipoxide and hereafluoroacetane, but the present reaction as shown in Example 2 is more efficient and uses less expensive starting materials.

The second method for the preparation of the subject compound involves the reaction 2,2-bis(trifluoromethyl) -4-iodo-4,5,5-trifluoromethyl-1,3-dioxolane with zinc in acetic anhydride ($Ac_2O$) and methylene chloride. The reaction can be represented by the following formula:

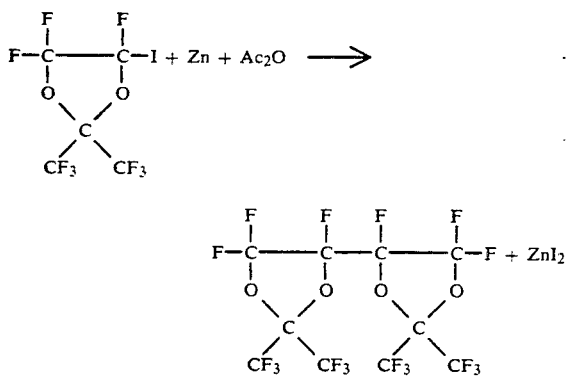

Generally, the reaction is carried out at from 25° to 40° C. The pressure is not critical and at nominal atmospheric pressure is normally used. Generally, starting material of an inert diluent such as acetic anhydride is used. The zinc preferably is in powdered form and is used in an amount of 0.8 to 1.5 the stochiometric amount needed to complete the reaction but 1.0 time the stochiometric amount is preferred. Generally, the product is recovered by filtering out zinc iodide and unreacted zinc followed by distillation to separate the product.

Fluorine atoms give a clear nuclear magnetic resonance signal. There is essentially no $^{19}F$ signal in body tissue. Therefore, when atoms are in the correct molecular environment in a compound that has the proper physical and biological properties, they can serve as diagnostic probes to delineate open spaces in body tissue or organs. Perfluoro-4,4'-bis(2,2-dimethyl-1,3-dioxolane) is such a compound. It has an excellent $^{19}F$ magnetic resonance signal, over 80% of its fluorine atoms are within a narrow signal range which results in an excellent signal to noise ratio eliminating chemical shift artifacts in $^{19}F$ image. Further, it has the proper physical properties for biological use. Compounds with too low a boiling point tend to form embolisms when injected into the body. The approximately 30° C. boiling point of perfluoro-4,4'-bis(2,2-dimethyl-1,3-dioxolane) minimizes this problem. Compounds with too large a molecular weight are not easily eliminated by the normal method of expiration, but tend to persist in the body for an indeterminately long time. The methyl-1,3-dioxolane) is ideal for this procedure.

The magnetogyric ratio of fluorine is close enough to that of hydrogen that existing imaging devices can be used with minor modification.

The prior compounds available for nuclear magnetic resonance imaging using signals from fluorine containing compounds suffer from various problems. Either the compounds contained fluorine atoms in various molecular environments resulting in multiple signals (low signal to noise ratio). It has been discovered in the present invention, a compound in which 80% of its fluorine atoms give the same magnetic signal, i.e., narrow signal.

In summary, the advantages of PBDD over perfluorooctyl bromide PFOB and (1,2-bis(perfluorobutyl ethylene), i.e., F-44E for MRI applications are: (1) the relatively longer $T_2$ relaxation time of PBDD compared to the imagable fluorine of PFOB and F-44E (i.e., the perfluorinated methylene groups) results in a factor of 2 increase in sensitivity at TE's of 10 msec; (2) the essentially single $^{19}F$ peak of PTRD eliminates chemical shift artifacts; (3) PBDD displays minimal J-modulation effects; and (4) $^{19}F$ imaging of PBDD requires no special hardware or software modifications to clinical instrumentation.

One aspect of the present invention can be practiced by preparing a suitable aqueous emulsion of perfluoro-4,4'-bis(2,2-dimethyl-1,3-dioxolane) for in-vivo injection into a body part such as by direct injection into a body cavity (thoric, peritoneal), direct injection into a body compartment, direct injection into a body space (subarachnoid), direct injection into a joint capsule, or direct injection into the bloodstream. It has been discovered in the present invention a compound that unexpectedly 80% of its fluorine atoms give the same magnetic signal, i.e., narrow signal.

The perfluoro-4,4'-bis(2,2-dimethyl-1,3-dioxolane) emulsions appear to be useful for nuclear magnetic resonance imaging to enhance the contrast between the cerebrospinal fluid, the brain and the spinal cord for diagnosis of tumors adjacent to the cerebrospinal fluid compartment, arachnoic cysts, cerebrospinal fluid rhinorrhea, otorrhes, papillomas, pineslomas, arachnoiditis, and internal hydrocephaly. Additional diagnostic areas of interest include cardiovascular blood transport, which can be observed for site blockage, gastrontestinal constrictions which can be outlined, lung capacity and tissue degeneration which can be located, and tumors which can be detected during early stages of tumor development.

The aqueous emulsion of perfluoro-4,4'-bis-(2,2-dimethyl-1,3-dioxolane) used for injection into the body generally contains from 5 to 40% v/u perfluoro-4,4'-bis(2,2-dimethyl-1,3-dioxolane), from 0.1 to 1% v/u of an emulsifying agent and 0.1 to 2.0% v/u of a buffer system to control the pH at 7 to 8. For most uses, the emulsion needs to be a physiologically acceptable aqueous medium. Suitable physiologically acceptable emulsifying agents include egg yolk lecithin, Pluronic F68, S'pan/two mixture and the like. Modified tyrodes solution is a suitable buffering system, but others such as saline or glycerine can be used.

In addition, the perfluoro-4,4'-bis(2,2-dimethyl-1,3-dioxodane) can be used as a solvent for fluoropolymers; in particular, the Teflon ®-AF.

EXAMPLE 1

Preparation of perfluoro-4,4'-bis(2,2-dimethyl-1,3-dioxolane) by fluorination of 4,4'-bis-[2,2-bis(trifluoromethyl)-1,3-dioxolane].

4,4'-bis[2,2-bis(trifluoromethyl)-1,3-dioxolane] (17 g, 0.042 mole) was mixed with 200 ml Krytox TM oil. This mixture was then poured into a fluorination reactor lined with fluorinated ethylene-propylene copolymer. The contents were irradiated by a 450 watt medium pressure Hanovia ultraviolet lamp from outside the reactor. A 1/4 inch ($6.35 \times 10^{-4}$m) outside diameter cooling coil was placed inside the reactor. Temperature of the contents were kept at about 8° C. during fluorination by passing water through the coil. The contents of the flask were first purged at 200 cc/min of nitrogen for one hour to remove air. Fluorine diluted with nitrogen was then added as follows:

$F_2/N_2$ in cc/min.; 10/50 for 30 min., 25/50 for 50 min., 35/50 for 60 min., 45/50 for 90 min., and 100/150 for 60 min.

The fluorinated products were purified by vacuum distillation at 70 mm Hg and a 135° C. pot temperature. The fraction boiling at 130° C. (4.33 g, 0.0082 mol was analyzed and found to be perfluoro-4,4'-bis(2,2-dimethyl-1,3-dioxolane). The yield based on 4,4'-bis[2,2-bis(trifluoromethyl)-1,3-dioxolane] was 19.6%. The $^{19}F$ NMR had peaks at $-81.5$ and $-115.8$ ppm. The relative intensity was 8:1.

EXAMPLE 2

Preparation of 4,4'-bis[2,2-bis(trifluoromethyl)-1,3-dioxolane].

A 42.0 g sample (0.2 mol) of 2,2-bis(trifluoromethyl)-1,3-dioxolane was stirred in a reactor under nitrogen with five drops of mercury and refluxed into a 28 mm O.D. quartz tube which was irradiated with a spiral low-pressure mercury lamp. Reaction was continued for 32.5 hours, during which time the boiling point rose from 106° C. to 155° C. Gas chromatography indicated 8.5 g (20%) of unreacted 2,2-bis(trifluoromethyl)-1,3-dioxolane to be present.

Fractionation of the mixture afforded 24.8 g (59% conversion, 74% yield) of the meso and racemic forms of 4,4'-bis[2,2-bis(trifluoromethyl)-1,3-dioxolane] boiling point 54°-100° C. (20 mm Hg).

The lower-boiling isomer solidified, mp 44.5°-46.0° c., IR (CCl4):2970 and 2923 (saturated CH, 1250-1100 cm$^{-1}$ (CF, C—O). NMR (CDCl3):1H 0 4.56 (M,2H, CH), 4.51 (M, 2H, 3H), 4.32 (M, 2H, CH); $^{19}F$ 0-80.5 (M, 3F, CF3,-80.6 (M, 3F, CF3). MS; m/e 349 (M+/2). For the higher boiling isomer, IR (CCl4):2980 and 2922 (saturated CH) 1250-1100 cm$^{-1}$ (CF, C—O). NMR (CDCl3):1H 0 4.61 (M, 2H, CH), 4.47 (M, 2H, CH), 4.22 (M, 2H, CH); $^{19}F$ 0-80.6 (rough q'd ff 7H2, 3F, CF3), $-81.0$ (q, Jff, 7H2, 3F, CF3). MS:similar to the other isomers.

EXAMPLE 3

Preparation of perfluoro-4,4'-bis(2,2-dimethyl-1,3-dioxolane) from 2,2-bis(trifluoromethyl)-4-iodo-4,5,5-trifluoro-1,3-dioxolane.

A solution of 2,2-bis(trifluoromethyl)-4-iodo-4,5,5-trifluoro-1,3-dioxolane, as prepared by Example 4 below, (19.5 g, 0.05 mole) in acetic anhydride (10.2 mole, 0.1 mole) was added to a suspension of 3.28 g zinc dust in 20 ml methylene chloride. The resulting mixture was stirred for 16 hours in a 200 ml flask at 30° C. for 16 hours. It was filtered and the bottom layer of filtrate was distilled to give 10 g (76% yield) of perfluoro-4,4'-bis(2,2-dimethyl-1,3-dioxolane) as a clear colorless liquid boiling point 30° C.

EXAMPLE 4

Preparation of 2,2-bis(trifluoromethyl)-4-iodo-4,5,5-trifluoro-1,3-dioxole made according to the process disclosed in U.S. patent application No. 07/450,351, the teachings of which is incorporated herein by reference.

A 400 ml Hastelloy C shaker tube was charged with a mixture of perfluoro-2,2-dimethyl-1,3-dioxole (48.8 g, 0.2 mole), mercury (II) oxide (45 g, 0.208 mole), iodine (127 g, 0.5 mole), phenothiazine (0.1 g) and hydroquinone (0.055 g). The tube was evacuated cold and hydrogen fluoride (12 g, 0.6 mole) was added to the tube. The tube was sealed and heated at 50° C. for two hours with shaking, the temperature was increased to 125° C. over a two hour period and maintained at this temperature for an additional three hours while continuing shaking. The resulting mixture was carefully added to ice water and the bottom layer separated. It was purified by distillation to give 50 g (64% yield) of 2,2-bis(trifluoromethyl)-4-iodo4,5,5-trifluoro-1,3-dioxolane, as a clear, color liquid, boiling point 74°-76° C.

EXAMPLE 5

Perfluoro-4,4'-bis(2,2-dimethyl-1,3-dioxolane) is a water-insoluble fluorochemical liquid which is emulsified in a physiologically acceptable aqueous medium for use herein using egg yolk lecithin as an emulsifier. No chemical reaction is involved in the process. A suitable stirred container is charged with 11.3 g modified Tyrode's solution, 0.9 g egg yolk lecithin and 13.6 g perfluoro-4,4'-bis(2,2-dimethyl1,3-dioxolane) to provide 20 ml of emulsion weighing 25.8 g and having a pH of 7.4. The modified Tyrode's solution used contained 6.7 g NaCl, 0.4 g KCl, 0.4 g CaCl$_2$.2H$_2$O, 2.3 g NaHCO$_3$, and 0.5 g MgCl$_2$.6H$_2$O diluted to 1,000 ml with sterile water. The egg yolk lecithin was commercially available and contained 70 wt% phosphatidyl chloride, 14 wt% phosphatidyl ethanolamine, 1.4 wt% bysophosphatidyl chlorine and 1.3 wt% water.

Nude mice, bearing H-MESO-1 human tumor xenographs, were administered 10 g/Kg of a 40% (v/v) aqueous emulsion of the above mixture of perfluoro-4,4'-bis(2,2-dimethyl-1,3-dioxolane)/water, via tail vein injection two hours prior to imaging. In vivo $^{19}F$ images were obtained on a GE Signa 1.5 T clinical instrument, operating at 60.13 MHz, using the standard spin-echo imaging database. A "birdcage" imaging coil was used to accommodate the mice for $^{19}F$ nuclear magnetic resonance imaging. Thick slice, coronal $^{19}F$ images (TR=1178 msec., TE=20 msec., FOV=8 cm, NEX=4, slice thickness of 20 mm, image resolution of 256×128, and a total experiment time of 15 minutes and 15 seconds) showed the bio-distribution of the perfluoro-4,4-bis(2,2-dimethyl-1,3-dioxolane) in the vasculature and reticuloendotheitial system.

EXAMPLE 6

C3H mice, bearing a RIF-1 murine tumor and weighing between 20 and 23 grams, were each administered 0.4 ml of the 40% (v/v) aqueous emulsion of perfluoro-4,4'-bis(2,2-dimethyl-1,3-dioxolane) emulsion described above via tail vein injection. In vivo $^{19}F$ images were obtained using the equipment described in Example 5. Single thick-slice, T1 weighted, spin-echo images (TR=2000 ms, TE=20 ms) were obtained using 2 averages, 128 phase-encode increments, and a 8 cm field of view (total experiment time of 3.4 minutes). Each of the 128 phase-encode steps were acquired with 4 averages, resulting in a total experiment time of 17.1 minutes. Two hours after injection, in addition to liver and spleen, perfluoro-4,4'-bis(2,2-dimethyl-1,3-dioxolane) was clearly present in the area of the tumor, in both coronal and sagittal views. After 24 hours, the signal from vascular perfluoro-4,4'-bis(2,2-dimethyl-1,3-dioxolane) subsided and the $^{19}F$ signal from the tumor was much more defined than the images obtained 2 hours after injection. These images clearly demonstrate the sequestering of perfluoro-4,4'-bis(2,2-dimethyl-1,3-dioxolane) in these tumors.

I claim:
1. Perfluoro-4,4'-bis(2,2-dimethyl-1,3-dioxolane).

* * * * *